(12) United States Patent
Sachse et al.

(10) Patent No.: US 7,253,903 B2
(45) Date of Patent: Aug. 7, 2007

(54) SYSTEM AND METHOD FOR DETERMINING GAS OPTICAL DENSITY CHANGES IN A NON-LINEAR MEASUREMENT REGIME

(75) Inventors: Glen W. Sachse, Yorktown, VA (US); Mauro Rana, Hampton, VA (US)

(73) Assignee: United States of America as represented by the Administrator of the National Aeronautics and Space Administration, Washington, DC (US)

( * ) Notice: Subject to any disclaimer, the term of this patent is extended or adjusted under 35 U.S.C. 154(b) by 177 days.

(21) Appl. No.: 11/027,930

(22) Filed: Dec. 29, 2004

(65) Prior Publication Data

US 2006/0139648 A1    Jun. 29, 2006

(51) Int. Cl.
    *G01N 21/00*    (2006.01)
(52) U.S. Cl. .......................... 356/437; 356/432
(58) Field of Classification Search ............... 250/343; 356/364, 437
    See application file for complete search history.

(56) References Cited

U.S. PATENT DOCUMENTS

| | | | |
|---|---|---|---|
| 4,443,791 A | 4/1984 | Risgin et al. | |
| 4,578,762 A * | 3/1986 | Wong | 702/32 |
| 4,730,479 A | 3/1988 | Pyke et al. | |
| 5,034,725 A | 7/1991 | Sorensen | |
| 5,341,214 A * | 8/1994 | Wong | 356/437 |
| 5,789,659 A | 8/1998 | Williams | |
| 5,841,137 A | 11/1998 | Whitney | |
| 6,008,928 A | 12/1999 | Sachse et al. | |
| 6,051,123 A | 4/2000 | Joshi et al. | |
| 6,057,923 A | 5/2000 | Sachse | |
| 6,289,288 B1 | 9/2001 | Kraft | |
| 6,360,582 B1 | 3/2002 | Chelvayohan et al. | |
| 6,574,031 B1 | 6/2003 | Sachse | |
| 6,611,329 B2 | 8/2003 | Sachse | |
| 6,688,159 B1 * | 2/2004 | Grunewald | 73/25.03 |
| 6,789,021 B2 | 9/2004 | Rendahl et al. | |
| 2003/0147080 A1 * | 8/2003 | Sarkis et al. | 356/437 |
| 2003/0206325 A1 | 11/2003 | Sachse et al. | |
| 2004/0156050 A1 | 8/2004 | Sachse et al. | |
| 2005/0253061 A1 * | 11/2005 | Cameron et al. | 250/287 |
| 2006/0047445 A1 * | 3/2006 | Williams et al. | 702/30 |

* cited by examiner

*Primary Examiner*—Gregory J. Toatley, Jr.
*Assistant Examiner*—Jarreas Underwood
(74) *Attorney, Agent, or Firm*—Helen M. Galus

(57) ABSTRACT

Each of two sensors, positioned to simultaneously detect electromagnetic radiation absorption along a path, is calibrated to define a unique response curve associated therewith that relates a change in voltage output for each sensor to a change in optical density. A ratio-of-responses curve is defined by a ratio of the response curve associated with the first sensor to the response curve associated with the second sensor. A ratio of sensor output changes is generated using outputs from the sensors. An operating point on the ratio-of-responses curve is established using the ratio of sensor output changes. The established operating point is indicative of an optical density. When the operating point is in the non-linear response region of at least one of the sensors, the operating point and optical density corresponding thereto can be used to establish an actual response of at least one of the sensors whereby the actual sensor output can be used in determining changes in the optical density.

3 Claims, 2 Drawing Sheets

SYSTEM AND METHOD FOR DETERMINING GAS OPTICAL DENSITY CHANGES IN A NON-LINEAR MEASUREMENT REGIME

ORIGIN OF THE INVENTION

The invention described herein was made in the performance of work under a NASA contract and by an employee of the United States Government and is subject to provisions of Section 305 of the National Aeronautics and Space Act of 1958, as amended, Public Law 85-568 (72 Stat. 435, 42 U.S.C. § 2457), and may be manufactured and used by or for the Government for governmental purposes without the payment of any royalties thereon or therefore.

BACKGROUND OF THE INVENTION

Field of the Invention

This invention relates to measuring gas concentration along a path. More specifically, the invention is a system and method for determining gas optical density changes in the non-linear measurement regime of gas concentration sensors.

SUMMARY OF THE INVENTION

In accordance with the present invention, a system and method are provided for determining gas optical density changes in the non-linear measurement regime of gas concentration sensors. The system and method utilize a gas concentration monitoring system that monitors concentration of a gas along a path irradiated by electromagnetic radiation. Absorption of at least some of the electromagnetic radiation at a specific wavelength by the gas is indicative of a measure of the concentration of the gas along the path. The gas concentration monitoring system includes first and second sensors positioned to simultaneously detect the electromagnetic radiation absorption along the path. Each of the first and second sensors are calibrated to define a unique response curve associated therewith that relates a change in voltage output for each sensor to a change in optical density. Each response curve includes a unique non-linear response region. A ratio-of-responses curve is formed and is defined by a ratio of the response curve associated with the first sensor to the response curve associated with the second sensor. Outputs from each of the first and second sensors are collected. A processor generates a ratio of sensor output changes using the outputs from each of the first and second sensors. The ratio of sensor output changes is defined as a ratio of output changes associated with the first sensor to output changes associated with the second sensor. An operating point on the ratio-of-responses curve is established using the ratio of sensor output changes. The established operating point is indicative of an optical density. When the operating point is in the non-linear response region of at least one of the first and second sensors, the operating point and optical density corresponding thereto can be used to establish an actual response of at least one of the first and second sensors whereby the actual sensor output can be used in determining changes in the optical density.

DETAILED DESCRIPTION

Figure 1:
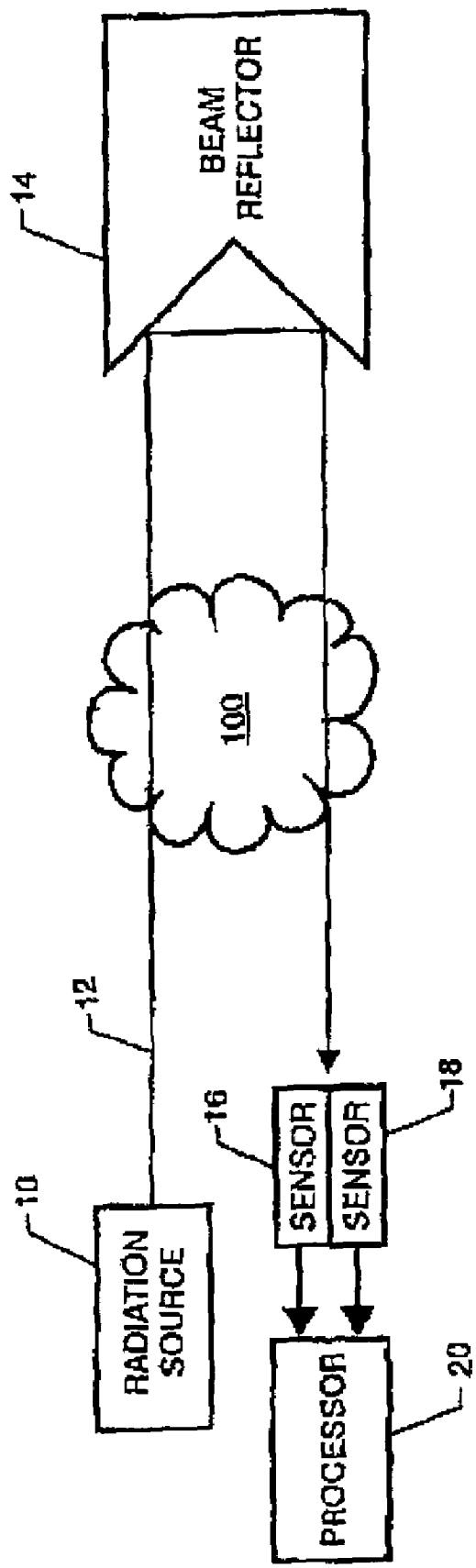
FIG. 1 is a block diagram of one embodiment of a gas concentration monitoring system that can be used to determine gas optical density changes of gas sensors operating in a non-linear measurement regime in accordance with the present invention.

Before describing the embodiment in detail, the operating principles of a beam absorption-type gas sensing system for measuring transient changes in gas concentration will be briefly outlined. Such sensors are often operated in a "balanced" or "zeroed" configuration that maximizes their sensitivity to transient changes. In effect, these sensors nullify the absorption from the background or ambient level of the gas of interest along the beam path. By operating this way, such sensors are optimized to sense minute changes in gas concentration along the optical path and not the steady-state concentration of the gas of interest along the path.

Many gas concentration sensing or determining systems (e.g., systems used in vehicle exhaust measurement, smoke stack exhaust measurement, air quality monitoring, breath analysis, etc.) transmit a beam of electromagnetic radiation (e.g., infrared, visible, ultraviolet, etc.) through a gaseous region of interest. Molecular absorption bands of the various gases present in the gaseous region absorb energy from the beam with each gas being absorbed in a specific spectral region. As the gas volume (or plume) of interest crosses the beam path, a change in sensor output voltage is recorded that is proportional to the percentage change in beam absorption (as viewed by the sensor) within one of the corresponding specific spectral regions. The change in sensor output is in response to a change in optical density of that gas in the gaseous region. The parameter "optical density" is defined as the integrated product of concentration of a gas of interest times the interaction path length of the beam with the gas of interest. The complex absorption bands of gas molecules yield a complicated, non-linear relationship between beam absorption and gas optical density. This non-linear relationship between absorption and optical density impacts the accuracy of such gas-sensing measurements.

Some measurement applications reference the change in optical density of a specific gas to the corresponding optical density change from a reference gas present in the gas volume of interest. Examples of such applications include cross-road vehicle exhaust measurements and breath analysis. Remote vehicle exhaust measurements are discussed further herein as an example without limiting the scope of the embodiment.

A remote vehicle exhaust measurement typically seeks to determine the concentration of specific gases at the tailpipe of a motor vehicle. Tailpipe concentrations of certain gas pollutants, such as carbon monoxide, nitric oxide, and total hydrocarbons, are often used to determine if a motor vehicle meets or fails emission standards. A cross-road optical path intersects the exhaust plume after it exits the tailpipe and experiences dilution by ambient air. Within the plume, the spatial distribution of exhaust gas concentrations is complex and undetermined. Given this setting, an exhaust measurement system cannot derive pollutant tailpipe concentrations unless additional information is available. Fortunately, carbon dioxide (i.e., a major combustion product not considered to be a pollutant) has a tailpipe concentration that is known through straight-forward, stoichiometry-based calculations.

In addition, the spatial distribution of the carbon dioxide exhaust is identical to the spatial distribution of other exhaust products. Therefore, by determining the optical density change of each pollutant gas and that of carbon dioxide, a tailpipe concentration for each pollutant gas may be calculated. The simultaneous detection of carbon dioxide enables such a measurement application. Furthermore, the accuracy of all tailpipe pollutant concentration measurements depends on the accuracy with which the carbon dioxide optical density change is determined. Because of the importance of this specific gas measurement to this embodiment, its measurement will now be discussed in greater detail without limiting the scope of the embodiment.

In vehicle exhaust measurement systems, the carbon dioxide measurement is typically made in the 4.2 to 4.45 micron carbon dioxide absorption band. Because this band is a strong molecular absorption band and carbon dioxide exhaust emissions are relatively high, vehicular carbon dioxide measurements generally possess a high signal-to-noise (S/N) ratio (i.e., the ratio of the absorption signal magnitude to random or pseudo-random instrument noise sources such as detector noise). A greater source of measurement error or inaccuracy may be related to the non-linearity of the measurement. Because ambient (i.e., background) levels of carbon dioxide are relatively high (i.e., even "clean air" values are currently ~375 ppmv) and because the absorption band of carbon dioxide is strong, individual carbon dioxide lines are in various stages of spectral saturation. Thus, the integrated absorption across the band is non-linear with respect to optical density. This non-linearity is aggravated in polluted atmospheres (e.g., urban roadways) where carbon dioxide levels can be substantially greater than "clean air" levels. The magnitude of the background optical density impacts the degree of non-linearity between beam absorption and optical density. Because the cross-road sensor detects changes in beam absorption, a failure to account for this non-linear behavior impacts the accuracy of determining the change in optical density which, in turn, affects the ability to accurately determine tailpipe concentrations of exhaust pollutants.

Though this discussion highlights spectral saturation and non-linearity associated with carbon dioxide in remote exhaust measurements, other vehicular exhaust gases (e.g. carbon monoxide) may also experience similar non-linear behavior due to high build-up of ambient carbon monoxide across the roadway.

Referring now to the drawings and more particularly to FIG. 1, one type of a gas concentration measurement system used in the present embodiment includes a radiation source 10 for generating a beam 12 of electromagnetic radiation, a beam reflector 14, and gas sensors 16 and 18. Beam reflector 14 is positioned to reflect beam 12 back toward sensors 16 and 18 after beam 12 passes through a gaseous region of interest 100. Thus, the path length traversed by beam 12 includes the distance from radiation source 10 to beam reflector 14 plus the distance from beam reflector 14 to sensors 16 and 18. The outputs of sensors 16 and 18 are provided to a processor 20 that can be used to implement the present embodiment as will be described further below.

Figure 2:
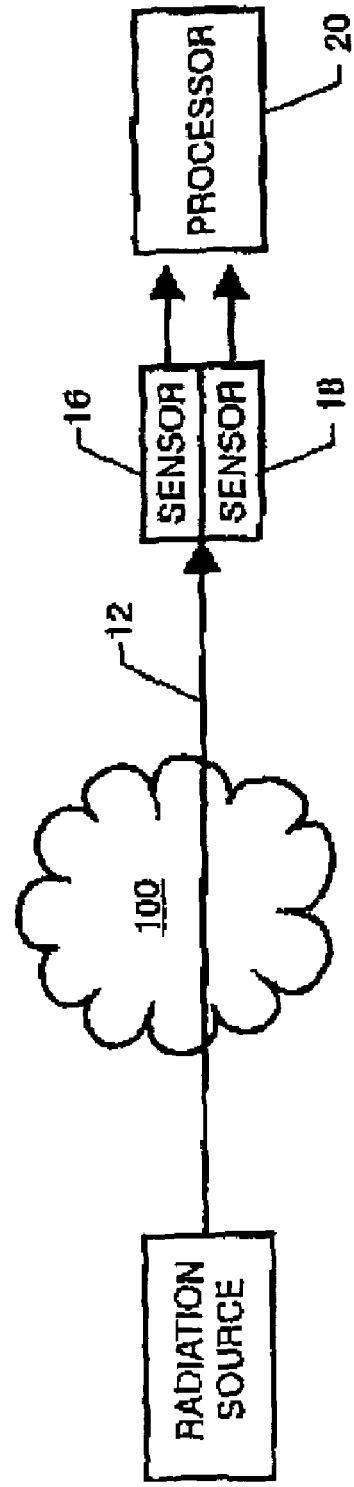
FIG. 2 is a block diagram of another embodiment of a gas concentration monitoring system that can be used to determine gas optical density changes of gas sensors operating in a non-linear measurement regime in accordance with the present invention.

The present invention is not limited to use of the retro-reflective embodiment shown in FIG. 1. For example, FIG. 2 illustrates another embodiment of a gas concentration measuring system that may be used in which radiation source 10 transmits its beam 12 through region of interest 100 where it then impinges on sensors 16 and 18. In this system, the path length traversed by beam 12 only extends from radiation source 10 to sensors 16 and 18.

Figure 3:
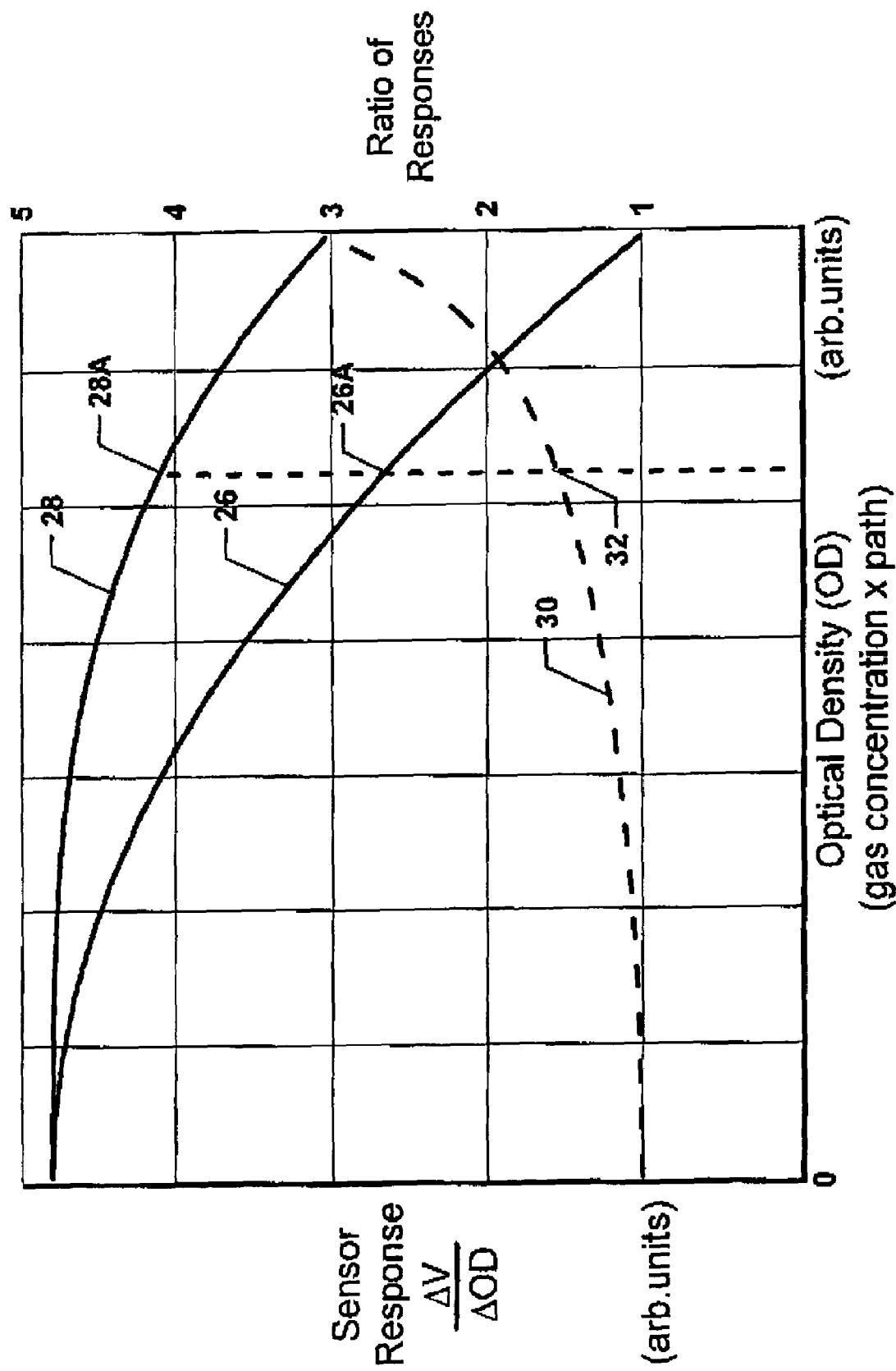
FIG. 3 is a graph of typical response curves for the gas sensors of the monitoring system of FIG. 1 or FIG. 2 and the ratio of responses curve for use in the method of determining gas optical density changes of the gas sensors operating in a non-linear measurement regime in accordance with the present invention.

Each of sensors 16 and 18 (in either the FIG. 1 or FIG. 2 measurement system) are positioned and operated to simultaneously detect gas absorption along the same particular path of beam 12. The positions of sensors 16 and 18 as well as optics that may be used to create such simultaneous detection of beam 12 are well understood in the art. In addition to being positioned for the simultaneous detection of beam 12, sensors 16 and 18 should have a unique response curve associated therewith. More specifically, sensors 16 and 18 should have unique non-linear responses (i.e., ratio of sensor output change to optical density change) as a function of optical density (of the gas being monitored) as depicted in FIG. 3, wherein curve 26 is the response for sensor 16 and curve 28 is the response for sensor 18. Also plotted in FIG. 3 is a ratio-of-responses curve 30 where each point thereon is defined as the response value of curve 28 divided by the response value of curve 26 at the same optical density. Because curves 26 and 28 can be determined or calibrated for the particular sensors 16 and 18, ratio-of-responses curve 30 can be determined before field use of the gas concentration measurement system. Curves 26, 28 and 30 are stored in processor 20 (FIGS. 1 and 2), which is programmed to implement the following method.

With the situation depicted in FIG. 3 (i.e., two different sensors with different non-linearity properties simultaneously sensing changes in gas concentration along the same path), the observed or actual change in absorption signals measured by sensors 16 and 18 to the same stimulus (i.e., a gas plume 100 intersecting beam 12) over a measurement interval is recorded and then ratioed. The optical density change is the same for sensor 16 and 18 due to the common stimulus. Thus, the ratio of sensor voltage output changes is equivalent to the ratio-of-responses curve 30 of the two sensors. This actual or observed ratio can then be "looked up" on ratio-of-responses curve 30. Provided that at least one of sensors 16 and 18 is in the non-linear region of its response curve, a unique operating point (e.g., point 32) is defined on ratio-of-responses curve 30. From operating point 32, the total-path optical density can be inferred and the respective responses for sensors 16 and 18 (i.e., represented by points 26A and 28A respectively) at that optical density can be determined from curves 26 and 28. Once the operating point is known, the correct response from either sensor may be used to determine the optical density change from the change in sensor output over a measurement interval. That is, the response for sensor 16 and output from sensor 16 can be used to derive the change in optical density, or the response for sensor 18 and output from sensor 18 can be used to derive the change in optical density. This technique of determining the operating point (and thus the correct sensor response) is particularly suited for measurement applications where the signal-to-noise ratio is relatively high yet measurement non-linearity can contribute to inaccuracy.

Because both sensors 16 and 18 can be used to derive the change in optical density, the embodiment enables some strategy in determining which sensor measurement has the greatest signal-to-noise ratio. For example, the more strongly saturated sensor would yield a weaker change in output signal and likely poorer signal-to-noise ratio. Using a slightly more advanced statistical analysis, the information from both sensors could be used with the measurement from each sensor being weighted differently.

One application of the present embodiment is in the field of vehicular exhaust sensing. In this application, the two sensors could be a gas filter correlation radiometer (or GFCR sensor as it will be referred to hereinafter) and a differential absorption radiometer (or DAR sensor as it will be referred to hereinafter) to detect carbon dioxide. Thus, a system using two such sensors can have the sensor outputs processed in accordance with the present embodiment to provide reliable carbon dioxide measurements even when the sensors are operating in non-linear regimes. The present embodiment corrects for non-linearity by using an operating point on the sensors' response curves determined from data taken exactly along the optical measurement path. This operating point is refreshed each time a new measurement is made such as each time a new vehicle passes by the vehicular exhaust measurement system.

When used as part of a vehicular exhaust measurement system, another application of the present embodiment is the determination of average cross-road concentration of carbon dioxide during the time that the exhaust sensors are operational. Furthermore, through the use of emission indices (i.e., the ratio of tailpipe concentrations of a pollutant to carbon dioxide) measured for vehicular traffic, the road-level buildup of other exhaust gases may also be inferred. Such information may be valuable to a variety of studies including the health effects on drivers from exposure to accumulated vehicular exhaust (along roadways) that is circulated through the interior passenger compartment of a motor vehicle.

Another embodiment of the method described is its use in other open path measurement systems that are optimized for measuring changes in optical density. More specifically, in these open path systems, two (or more) simultaneous measurements are made using sensors having different non-linearity properties. The average absolute concentration of the gas of interest along the path may be inferred by noting the relationship of the changes in the two (or more) sensor signal amplitudes as the gas concentration varies on its own along the optical path. (Note that if the average concentration of the gas of interest across the path is relatively constant, artificial concentration variations may be induced by introducing a puff of the target gas into the optical path or by flowing the target gas through a cell placed in the beam path). Sensing the ratio of responses by the two (or more) simultaneous measurements enables the determination of the average concentration across the path.

Other applications of the embodiment include long open path measurement systems of carbon monoxide in urban or non-urban areas that provide regionally-averaged indicators of air quality. The teachings of the present embodiment are applicable because such long path lengths and potentially high carbon monoxide values would increase the likelihood of spectral saturation of the gas sensors and thereby contribute to non-linear measurements. The embodiment may also be applied to open-path monitoring systems inside industrial smoke stacks.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims. In the claims, means-plus-function and step-plus-function clauses are intended to cover the structures or acts described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures.

What is claimed as new and desired to be secured by Letters Patent of the United States is:

1. A system comprising:
   a gas concentration monitoring system that monitors concentration changes of a gas along a path irradiated by electromagnetic radiation, wherein a change of absorption of at least some of said electromagnetic radiation at a specific wavelength by said gas is indicative of a measure of said concentration changes of said gas along said path,
   said gas concentration monitoring system including first and second sensors positioned to simultaneously detect said absorption along said path,
   each of said first and second sensors being calibrated to thereby define a unique response curve associated therewith that relates a voltage output change per optical density change for each of said first and second sensors as a function of optical density,
   wherein each said response curve includes a unique non-linear response region thereof, and
   wherein a ratio-of-responses curve is defined by a ratio of said response curve associated with said first sensor to said response curve associated with said second sensor; and
   a processor coupled to said gas concentration monitoring system for generating a ratio of sensor output changes defined as a ratio of output changes associated with said first sensor to output changes associated with said second sensor, said ratio of sensor output changes being used to establish an operating point on said ratio-of-responses curve that is indicative of an optical density wherein, when said operating point is in said non-linear response region of at least one of said first and second sensors, said operating point and said optical density corresponding thereto can be used to establish an actual response of at least one of said first and second sensors that is used in determining changes in said optical density.

2. A system as in claim 1 wherein said first sensor is a gas filter correlation radiometer and said second sensor is a differential absorption radiometer.

3. A method comprising the steps of:
   providing a gas concentration monitoring system that monitors concentration of a gas along a path irradiated by electromagnetic radiation, wherein absorption of at least some of said electromagnetic radiation at a specific wavelength by said gas is indicative of a measure of said concentration of said gas along said path, said gas concentration monitoring system including first and second sensors positioned to simultaneously detect said absorption along said path;
   calibrating each of said first and second sensors to thereby define a unique response curve associated therewith that relates a change in voltage output for each of said first and second sensors to a change in optical density, wherein each said response curve includes a unique non-linear response region thereof;

forming a ratio-of-responses curve defined by a ratio of said response curve associated with said first sensor to said response curve associated with said second sensor;

collecting outputs from each of said first and second sensors;

generating a ratio of sensor output changes using said outputs from each of said first and second sensors, said ratio of sensor output changes defined as a ratio of output changes associated with said first sensor to output changes associated with said second sensor;

establishing an operating point on said ratio-of-responses curve using said ratio of sensor output changes, said operating point being indicative of an optical density wherein, when said operating point is in said non-linear response region of at least one of said first and second sensors, said operating point and said optical density corresponding thereto can be used to establish an actual response of at least one of said first and second sensors that is used in determining changes in said optical density; and utilizing said indicated optical density to monitor the concentration of said gas.

* * * * *